US012668576B2

(12) United States Patent
Cheng et al.

(10) Patent No.: US 12,668,576 B2

(45) Date of Patent: Jun. 30, 2026

(54) PYRAZOLAMIDE DERIVATIVE, PREPARATION METHOD THEREFOR, AND APPLICATION THEREOF

(71) Applicant: SHENZHEN ZHONGGE BIOLOGICAL TECHNOLOGY CO., LTD., Guangdong (CN)

(72) Inventors: Huimin Cheng, Guangdong (CN); Xiaoming Wen, Guangdong (CN); Peiyu Zhang, Guangdong (CN); Zhiqiang Liu, Guangdong (CN); Lan Luo, Guangdong (CN); Lipeng Lai, Guangdong (CN); Jian Ma, Guangdong (CN); Shuhao Wen, Guangdong (CN)

(73) Assignee: SHENZHEN ZHONGGE BIOLOGICAL TECHNOLOGY CO., LTD., Guangdong (CN)

( * ) Notice: Subject to any disclaimer, the term of this patent is extended or adjusted under 35 U.S.C. 154(b) by 531 days.

(21) Appl. No.: 18/274,093

(22) PCT Filed: Jan. 27, 2022

(86) PCT No.: PCT/CN2022/074141

§ 371 (c)(1),
(2) Date: Jul. 25, 2023

(87) PCT Pub. No.: WO2022/161418

PCT Pub. Date: Aug. 4, 2022

(65) Prior Publication Data

US 2024/0409516 A1 Dec. 12, 2024

(30) Foreign Application Priority Data

Jan. 28, 2021 (CN) ......................... 202110118872.8

(51) Int. Cl.
*C07D 231/20* (2006.01)
*A61K 31/415* (2006.01)

(52) U.S. Cl.
CPC .......... *C07D 231/20* (2013.01); *A61K 31/415* (2013.01)

(58) Field of Classification Search
CPC ............................ C07D 231/20; A61K 31/415
See application file for complete search history.

(56) References Cited

U.S. PATENT DOCUMENTS

2023/0125494 A1* 4/2023 Zhang ....................... A61P 3/00
514/407

FOREIGN PATENT DOCUMENTS

| | | | |
|---|---|---|---|
| CN | 1867551 | A | 11/2006 |
| CN | 103097358 | A | 5/2013 |
| CN | 106572993 | A | 4/2017 |
| CN | 113354585 | A | 9/2021 |
| WO | 2005021508 | A1 | 3/2005 |
| WO | 2012039972 | A1 | 3/2012 |
| WO | 2015179615 | A1 | 11/2015 |
| WO | 2021175283 | A1 | 9/2021 |

OTHER PUBLICATIONS

Sowaileh M.F. et al., "Application of the Pentafluorosulfanyl Group as a Bioisosteric Replacement", ChemMedChem 12:1481-1490 (Sep. 14, 2017).
Chinese Notice of Grant dated Aug. 1, 2025 received in Chinese Application No. 202280011067.8, together with an English-language translation.
International Search Report dated Mar. 29, 2022 issued in PCT/CN2022/074141.

* cited by examiner

*Primary Examiner* — Kamal A Saeed

(74) *Attorney, Agent, or Firm* — Scully, Scott, Murphy & Presser, P.C.

(57) ABSTRACT

The present invention relates to a compound of chemical Formula (I), a preparation method therefor, and an application thereof, as well as a pharmaceutical composition comprising the compound as an active ingredient, or a pharmaceutically acceptable salt thereof. The present invention further relates to a use of the compound of Formula (I) in the treatment and prevention of $EP_4$-mediated diseases.

(I)

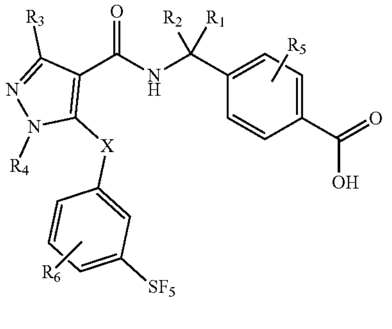

10 Claims, No Drawings

PYRAZOLAMIDE DERIVATIVE, PREPARATION METHOD THEREFOR, AND APPLICATION THEREOF

TECHNICAL FIELD

The present invention belongs to the field of medicine, and in particular relates to a class of heterocyclic amide derivatives and pharmaceutically acceptable salts thereof as $EP_4$ receptor antagonists, and pharmaceutical compositions using the same as active ingredients. The present invention also provides a method for preparing the compounds and an application of the same as a medicament for treating a disease mediated by prostaglandin E.

BACKGROUND ART

Upon encountering an antigen, naive CD4+ T helper precursor (Thp) cells differentiate into two distinct subtypes, i.e., T helper type 1 (Th1) and T helper type 2 (Th2). In recent years, a novel T cell subtype, Th17 cell, has also been identified and characterized. These differentiated Th cells are defined by their distinct functions and unique cytokine profiles. In contrast, Th2 cells are known to produce IL-4, IL-5, IL-6, IL-9, IL-10, and IL-13, which are responsible for potent antibody production, eosinophil activation, and inhibition of several functions of macrophages, thereby providing a phagocyte-independent protective response. Th17 cells mainly produce IL-17A, IL-17F, IL-21, IL-22 and TNF, are essential for host defense against extracellular pathogens, and are key mediators of autoimmunity. Thus, Th1, Th2 and Th17 cells are associated with different immunopathological responses.

The characteristics and therapeutic utility of prostaglandin receptors and their most commonly used selective agonists and antagonists have been extensively studied.

Prostaglandins are mediators of pain, fever, and other symptoms associated with inflammation. Prostaglandin $E_2$ ($PGE_2$) is the major metabolite of eicosanoids associated with inflammation. In addition, prostaglandin $E_2$ is also involved in various physiological and/or pathological symptoms, such as hyperalgesia, uterine contraction, digestive tract peristalsis, arousal, inhibition of gastric acid secretion, blood pressure, platelet function, bone metabolism, angiogenesis and so on. The four subtypes of prostaglandin $E_2$ receptors (EP1, EP2, EP3 and EP4) exhibit different pharmacological properties.

Compared to other prostaglandin receptors, the $EP_4$ receptor is characterized by the longest intracellular C-terminal loop. The $EP_4$ receptor is coupled to G protein and mediates elevated concentration of cyclic adenosine monophosphate. The expression of $EP_4$ receptor is controlled by various physiological and pathophysiological processes, as the receptor is involved in ovulation and fertilization, induction of bone formation, T cell cytokine signaling, prevention of inflammatory bowel disease, promotion of Langerhans cell migration and maturation, and mediates joint inflammation as well as other processes in a collagen-induced arthritis model.

Research has shown that prostaglandins regulate different phases of the immune response. $PGE_2$ stimulation via EP4 subtype of $PGE_2$ receptor can also have an opposite effect, i.e., promoting Th1 differentiation and IL-17 production in activated CD4+ cells. Meanwhile, the antagonism of EP4 with a novel selective EP4 antagonist or $PGE_2$-neutralizing antibody inhibits Th1 differentiation, Th17 proliferation, and IL-23 secretion of activated dendritic cells. The induction of Th1 differentiation by $PGE_2$ is mediated by PI3K signaling, while the stimulation of IL-17 production requires cAMP signaling. Additionally, administration of an EP4 antagonist to DBA/1 or C57BL/6 mice could suppress innate and adaptive immune responses and suppress diseases in collagen-induced arthritis (CIA) models and experimental autoimmune encephalomyelitis (EAE) models, thus demonstrating that $PGE_2$/EP4 signaling is critically involved in autoimmune pathology, suggesting that inhibition of $PGE_2$/EP4 signaling may show a therapeutic value in ameliorating inflammatory autoimmune diseases (e.g., rheumatoid arthritis and multiple sclerosis).

Accordingly, the compounds disclosed in the present invention are expected to be therapeutically useful in the treatment of diseases or conditions mediated by EP4 receptors in mammals such as humans, including but not limited to rheumatoid arthritis and multiple sclerosis.

There remains a need in the art for novel compounds that can effectively and reliably inhibit $EP_4$ in vitro and in vivo.

SUMMARY OF THE INVENTION

The object of the present invention is to provide a new class of novel compounds with $EP_4$ receptor inhibitory activity and/or good pharmacodynamic/pharmacokinetic properties and their use for treating or alleviating a prostaglandin E-mediated disease.

The first aspect of the present invention provides a compound of Formula I or a pharmaceutically acceptable salt, a hydrate, a solvate, a stereoisomer, an isotopic compound or a prodrug thereof, (I)

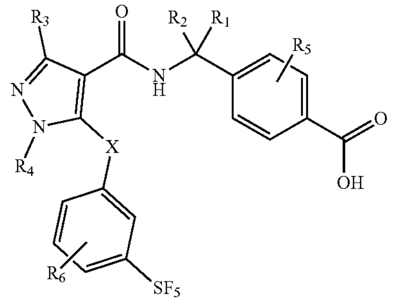

wherein, $R_1$ and $R_2$ are each independently selected from the group consisting of: H, unsubstituted or halogen-substituted $C_1$-$C_4$ alkyl;

or $R_1$ and $R_2$ form a $C_3$-$C_6$ cycloalkyl together with the carbon atom to which they are connected;

$R_3$ is unsubstituted or halogen-substituted $C_1$-$C_4$ alkyl;

$R_4$ is unsubstituted or halogen-substituted $C_1$-$C_4$ alkyl;

$R_5$ is selected from the group consisting of: hydrogen, halogen, $C_1$-$C_4$ alkyl and $C_1$-$C_4$ alkoxy; and $R_6$ is absent or selected from the group consisting of: halogen, unsubstituted or halogen-substituted $C_1$-$C_4$ alkyl, and unsubstituted or halogen-substituted $C_1$-$C_4$ alkoxy.

In another preferred embodiment, one of $R_1$ and $R_2$ is H, and the other is unsubstituted or halogen-substituted $C_1$-$C_4$ alkyl.

In another preferred embodiment, one of $R_1$ and $R_2$ is H, and the other is $CH_3$.

In another preferred embodiment, $R_3$ is methyl, monofluoromethyl, difluoromethyl or trifluoromethyl.

In another preferred embodiment, $R_4$ is methyl.

In another preferred embodiment, $R_5$ is hydrogen.

In another preferred embodiment, $R_6$ is absent, or is chlorine, fluorine, methyl, monofluoromethyl, difluoromethyl, trifluoromethyl or methoxy.

In another preferred embodiment, the prodrug is an ester formed by the compound of Formula I and $C_1$-$C_4$ alkyl-OH.

In another preferred embodiment, $R_1$, $R_2$, $R_3$, $R_4$, $R_5$ and $R_6$ are each independently the corresponding group in Compounds 1 to 3 of the present invention.

In another preferred embodiment, the compound of Formula I is selected from the group consisting of:

1

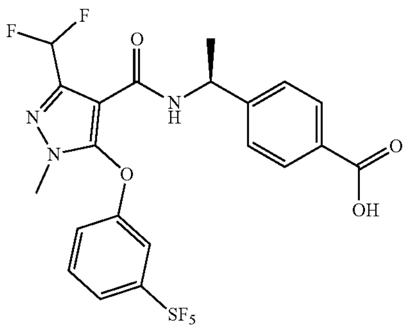

2

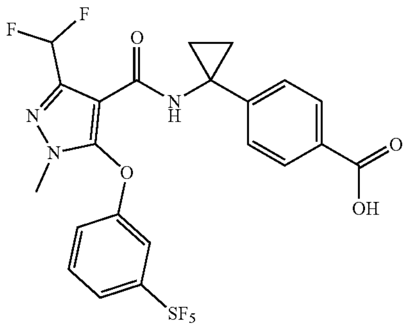

3

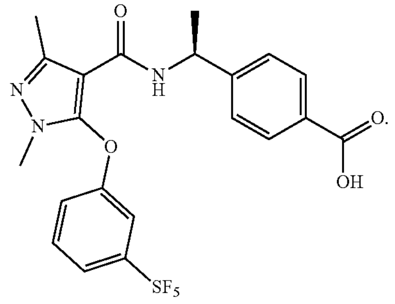

The second aspect of the present invention provides a pharmaceutical composition, which comprises the compound or a pharmaceutically acceptable salt, a hydrate, a solvate, a stereoisomer, an isotopic compound or a prodrug thereof as described in the first aspect, and a pharmaceutically acceptable carrier or diluent.

The third aspect of the present invention provides a use of the compound or a pharmaceutically acceptable salt, a hydrate, a solvate, a stereoisomer, an isotopic compound or a prodrug thereof as described in the first aspect or the pharmaceutical composition as described in the second aspect in the manufacture of a medicament for inhibiting EP4 receptor activity in a cell or a subject.

The fourth aspect of the present invention provides a use of the compound or a pharmaceutically acceptable salt, a hydrate, a solvate, a stereoisomer, an isotopic compound or a prodrug thereof as described in the first aspect or the pharmaceutical composition as described in the second aspect in the manufacture of a medicament for preventing and/or treating a disease associated with EP4 receptor.

In another preferred embodiment, the disease associated with EP4 receptor is selected from the group consisting of: acute and chronic pain, osteoarthritis, rheumatoid arthritis and cancer.

In another aspect, the present invention provides a method for treating a disease associated with EP4 receptor, the method comprising administering to a subject in need thereof a therapeutically effective amount of the compound or a pharmaceutically acceptable salt, a hydrate, a solvate, a stereoisomer, an isotopic compound or a prodrug thereof as described above, or the pharmaceutical composition as described above.

In another preferred embodiment, the subject is identified or diagnosed as having a disease associated with EP4 receptor.

In another preferred embodiment, the cell is a mammalian cell.

In another preferred embodiment, the subject is a mammal, preferably a human, a mouse, or a rat.

It should be understood that within the scope of the present invention, the above-mentioned technical features of the present invention and the technical features specifically described hereinbelow (e.g., examples) may be combined with each other to form new or preferred technical solutions. Due to space limitations, they will not be repeated herein.

DETAILED DESCRIPTION OF THE INVENTION

After extensive and in-depth research, through a large number of screening and testing, the inventors have found a class of compounds with EP4 receptor inhibitory activity. Furthermore, the compounds of the present invention have good pharmacodynamic/pharmacokinetic properties. On this basis, the present invention has been accomplished.

Terms

Unless defined otherwise, all technical and scientific terms used herein have the same meaning as commonly understood by one of ordinary skill in the art to which the present invention belongs.

As used herein, the term "comprise" or "include (contain)" may be in open, semi-closed and closed forms. In other words, the term also includes "consisting essentially of . . . ", or "consisting of . . . ".

When a substituent is described by a conventional chemical formula written from left to right, the substituent also includes chemically equivalent substituents obtained when the structural formula is written from right to left. For example, $—CH_2O—$ is equivalent to $—OCH_2—$.

The term "alkyl" by itself or as part of another substituent refers to a straight or branched chain hydrocarbon group having the indicated number of carbon atoms (i.e., $C_1$-$C_6$ means one to six carbon atoms). Examples of alkyl include, but are not limited to, methyl, ethyl, n-propyl, isopropyl, n-butyl, tert-butyl, isobutyl, sec-butyl, n-pentyl, n-hexyl, and the like. One or more positions in the alkyl may be substituted, especially by 1 to 4 substituents, and may be substituted at any position.

The term "halogen-substituted alkyl" or "haloalkyl" refers to a branched and straight chain saturated aliphatic hydrocarbon group having the indicated number of carbon atoms and being substituted with one or more halogens. Examples of halogen-substituted alkyl, but are not limited to, fluoromethyl, difluoromethyl, trifluoromethyl, trichloromethyl, pentafluoroethyl, pentachloroethyl, 2,2,2-trifluoroethyl, heptafluoropropyl and heptachloropropyl. Examples of halogen-substituted alkyl also include "fluoroalkyl" that is a branched and straight chain saturated aliphatic hydrocarbon group having the indicated number of carbon atoms and being substituted with one or more fluorine atoms.

The term "fluoroalkyl" refers to an alkyl as defined above, in which one or more hydrogen atoms are replaced by fluorine atoms.

The term "alkoxy" refers to —O-alkyl, and includes straight or branched or cyclic alkoxy, and representative examples thereof include (but are not limited to): methoxy, ethoxy, propoxy, isopropoxy and butoxy, etc. Preferred example is $C_1$-$C_3$ alkoxy.

The term "fluoroalkoxy" refers to an alkoxy as defined above, in which one or more hydrogen atoms are replaced by fluorine atoms.

The term "halogen-substituted alkoxy" or "haloalkoxy" refers to —O-haloalkyl, and includes straight or branched or cyclic haloalkoxy, and representative examples thereof include (but are not limited to): fluoromethoxy, difluoromethoxy, trifluoromethoxy, trichloromethoxy, pentafluoroethoxy, pentachloroethoxy.

The term "cycloalkyl" refers to a cyclic alkyl, including saturated monocyclic, bicyclic or polycyclic alkyl, such as $C_3$-$C_8$ or $C_3$-$C_{12}$ cycloalkyl, $C_3$-$C_8$ cycloalkyl refers to $C_3$, $C_4$, $C_5$, $C_6$, $C_7$, or $C_8$ cycloalkyl. Representative cycloalkyl groups of the present invention include, but are not limited to, cyclopropyl, cyclobutyl, cyclopentyl, cyclohexyl, and norbornyl.

The term "halo" or "halogen" includes fluorine, chlorine, bromine and iodine.

Unless otherwise stated, it is assumed that any heteroatom with non-full valence has sufficient hydrogen atoms to fill its valence.

When a substituent is a non-terminal substituent, it is a subunit of the corresponding group, for example, alkyl corresponds to alkylene, cycloalkyl corresponds to cycloalkylene, heterocyclyl corresponds to heterocyclylene, alkoxy corresponds to alkyleneoxy, etc.

The term "EP4 antagonist" refers to a compound that inhibits or blocks a cell signal transduction triggered by the interaction between $PGE_2$ and EP4 receptors, and includes but is not limited to the compound represented by Formula (I) described herein.

Active Ingredient

As used herein, the terms "compound of the present invention" and "active ingredient of the present invention" are used interchangeably and refer to a compound of Formula I, or a pharmaceutically acceptable salt, a hydrate, a solvate, a stereoisomer, an isotopic compound (e.g., deuterated compound) or a prodrug thereof. The terms also include racemate, optical isomer thereof.

The compound of the present invention has the structure shown in Formula I (I)

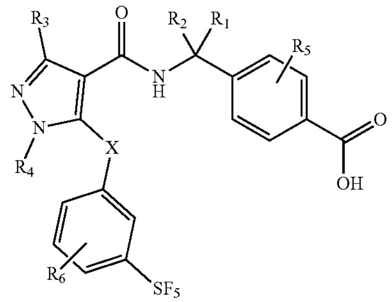

wherein, $R_1$, $R_2$, $R_3$, $R_4$, $R_5$ and $R_6$ are as defined above.

The salts that may be formed by the compound of the present invention also belong to the scope of the present invention. Unless otherwise stated, the compound of the present invention is understood to include its salts. The term "salt" as used herein refers to an acidic or basic salt formed with an inorganic or organic acid and a base. In addition, when the compound of the present invention contains a basic moiety which includes but is not limited to pyridine or imidazole or an acidic moiety which includes but is not limited to carboxylic acid, zwitterions ("inner salts") that may be formed are within the scope of term "salt". Pharmaceutically acceptable (i.e., non-toxic, physiologically acceptable) salts are preferred, while other salts are also useful, for example, in isolation or purification steps during preparation. The compound of the present invention may form a salt, for example, the compound I reacts with a certain amount, such as an equivalent amount, of acid or base, and a salt is precipitated from a medium, or freeze-dried in an aqueous solution.

The compound of the present invention which contains a basic moiety, including but not limited to amine or pyridine or imidazole ring, may form a salt with an organic or inorganic acid. Typical salts formed with acids include acetate (e.g., a salt formed with acetic acid or trihaloacetic acid such as trifluoroacetic acid), adipate, alginate, ascorbate, aspartate, benzoate, benzenesulfonate, bisulfate, borate, butyrate, citrate, camphorate, camphorsulfonate, cyclopentane-propionate, diglycolate, laurylsulfate, ethanesulfonate, fumarate, glucoheptonate, glycerophosphate, hemisulfate, heptanoate, hexanoate, hydrochloride, hydrobromide, hydroiodide, isethionate (e.g., 2-hydroxyethanesulfonate), lactate, maleate, methanesulfonate, naphthalenesulfonate (e.g., 2-naphthalenesulfonate), nicotinate, nitrate, oxalate, pectate, persulfate, phenylpropionate (e.g., 3-phenylpropionate), phosphate, picrate, pivalate, propionate, salicylate, succinate, sulfate (e.g., a salt formed with sulfuric acid), sulfonate, tartrate, thiocyanate, tosylate such as p-toluenesulfonate, dodecanoate, and the like.

Some compounds of the present invention which may contain an acidic moiety, including but not limited to carboxylic acid, may form a salt with various organic or inorganic bases. Typical salts formed with bases include ammonium salts, alkali metal salts such as sodium, lithium, potassium salts, alkaline earth metal salts such as calcium, magnesium salts, and salts formed with organic bases (e.g., organic amines), such as benzathine, dicyclohexylamine, hydrabamine (a salt formed with N,N-di(dehydroabietyl) ethylenediamine), N-methyl-D-glucamine, N-methyl-D- glucamide, tert-butylamine, and salts formed with amino acids such as arginine, lysine, etc. Basic nitrogen-containing groups may form quaternary ammonium salts with halides, such as small molecule alkyl halides (e.g., methyl, ethyl, propyl and butyl chlorides, bromides and iodides), dialkyl sulfates (e.g., dimethyl, diethyl, dibutyl, and dipentyl sulfates), long-chain halides (e.g., decyl, dodecyl, tetradecyl, and tetradecyl chlorides, bromides and iodides), aralkyl halides (e.g., benzyl and phenyl bromides), and the like.

All prodrugs and solvates of the compound of the present invention are contained by the present invention. Herein, the term "prodrug" refers to a compound that produces the compound, salt, or solvate of the present invention through metabolic or chemical transformation during the treatment of related diseases. The compound of the present invention includes solvate, such as hydrate.

As used herein, the term "solvate" refers to a complex in which the compound of the present invention coordinates with solvent molecules at a specific ratio.

As used herein, the term "hydrate" refers to a complex, such as monohydrate, formed by coordination of the compound of the present invention with water.

The compound of the present invention, or salt or solvate thereof, may have possible tautomeric forms (e.g., amide and imino ether). All such tautomers are part of the present invention.

All stereoisomers of the compound (for example, those with asymmetric carbon atoms possibly formed by various substitutions), including their enantiomeric and diastereomeric forms, are contained by the present invention. The individual stereoisomers of the compound of the present invention may not exist simultaneously with other isomers (for example, as a pure or substantially pure optical isomer having a specific activity), or may be a mixture, such as a racemate, or a mixture with all other stereoisomers or parts thereof. The chiral center of the present invention has two configurations, S or R, which are defined according to the 1974 proposal of the International Union of Pure and Applied Chemistry (IUPAC). The racemic form may be resolved by physical methods such as fractional crystallization, or by derivatization into diastereoisomers and then fractional crystallization, or by separation of chiral column chromatography. Individual optical isomers may be obtained from racemates by suitable methods, including but not limited to conventional methods such as salt formation with optically active acids followed by crystallization.

The compound of the present invention, obtained by preparation, separation and purification in sequence, has a weight content equal to or greater than 90%, for example, equal to or greater than 95%, equal to or greater than 99% ("very pure" compound), as described in the main text herein. Such "very pure" compound of the present invention is also included herein as part of the present invention.

All configurational isomers of the compounds of the present invention are contained by the scope of the present invention, whether in a mixture, pure or very pure form. The definition of the compound of the present invention includes both cis (Z) and trans (E) olefinic isomers, as well as cis and trans isomers of carbocyclic and heterocyclic rings.

Throughout the description, the groups and substituents may be selected to provide stable fragments and compounds.

Definitions of specific functional groups and chemical terms are detailed below. For purposes of the present invention, chemical elements are as defined in Periodic Table of the Elements, CAS version, *Handbook of Chemistry and Physics,* $75^{th}$ Ed, in which the definitions of specific functional groups are also described. In addition, the basic principles of organic chemistry and specific functional groups and reactivity are also described in "Organic Chemistry", Thomas Sorrell, University Science Books, Sausalito: 1999, and the entire contents of which are incorporated by reference.

Some compounds of the present invention may exist in particular geometric or stereoisomeric forms. The present invention covers all compounds, including their cis and trans isomers, R and S enantiomers, diastereomers, (D) isomers, (L) isomers, racemates and other mixtures. In addition, an asymmetric carbon atom may represent a substituent, such as an alkyl. All isomers, as well as mixtures thereof, are contained by the present invention.

According to the present invention, the mixture of isomers may contain various ratios of isomers. For example, in a mixture of only two isomers, there may be the following combinations: 50:50, 60:40, 70:30, 80:20, 90:10, 95:5, 96:4, 97:3, 98:2, 99:1, or 100:0, and all ratios of isomers are within the scope of the present invention. Similar ratios, as well as ratios that are mixtures of more complex isomers, that can be readily understood by one of ordinary skill in the art, are also within the scope of the present invention.

The present invention also includes isotopically labeled compounds, which are equivalent to the original compounds disclosed herein. In practice, however, substitution of one or more atoms by other atoms with different atomic mass or mass number usually occurs. Examples of isotopes that may be contained in the compound of the present invention include hydrogen, carbon, nitrogen, oxygen, phosphorus, sulfur, fluorine and chlorine isotopes, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$ and $^{36}Cl$. The compounds, or enantiomers, diastereomers, isomers, or pharmaceutically acceptable salts or solvates of the present invention that contain the above isotopes or other isotopic atoms are all within the scope of the present invention. Some compounds of the present invention labeled with radioactive isotopes such as $^{3}H$ and $^{14}C$ are useful in tissue distribution experiments for drugs and substrates. Tritium, namely $^{3}H$, and carbon-14, namely $^{14}C$, that are relatively easy to prepare and detect, are the first choice among isotopes. In addition, substitution of heavier isotopes such as deuterium, namely $^{2}H$, may be preferred in some cases, because there are advantages in certain therapies due to its good metabolic stability, such as increased half-life in vivo or reduced dosage. Isotopically-labeled compounds may be prepared in general methods by substituting a readily available isotopically-labeled reagent for a non-isotopically-labeled reagent, and using the protocols disclosed in the examples.

If the synthesis of a specific enantiomer of the compound of the present invention is to be designed, it may be prepared by asymmetric synthesis, or by derivatization with a chiral auxiliary, the resulting diastereomeric mixture is separated, and the chiral auxiliary is removed to obtain pure enantiomers. In addition, if the molecule contains a basic functional group, such as an amino acid, or an acidic functional group, such as a carboxyl group, it may be reacted with a suitable optically active acid or base to form a diastereomeric salt, and then separated by conventional means such as crystallization or chromatography to give pure enantiomers.

As described herein, the compound of the present invention may be substituted with any number of substituents or functional groups, thereby broadening the protection scope. Generally, whether the term "substitution" appears before or after the term "optional", the general formula of the present invention contains the formula of substituents, which means that a hydrogen radical is replaced by a specified structural substituent. When multiple positions in a specific structure are substituted with multiple specific substituents, the substituents may be the same or different for each position. The term "substitution" as used herein includes all permissible organic compound substitutions. Broadly speaking, the permissible substituents include acyclic, cyclic, branched and unbranched, carbocyclic and heterocyclic, aromatic and nonaromatic organic compound substituents. In the present invention, for example, heteroatom nitrogen may have hydrogen substituent or any permissible organic compound substituents as described above to complement its valence. Furthermore, the present invention is not intended to be limiting in any way to the organic compounds permissible to be substituted. Combinations of substituents and variable groups in the form of stable compounds are considered by the present invention to be beneficial in the treatment of diseases. The term "stable" herein means a compound that is stable, detectable for a sufficient period of time to maintain the structural integrity of the compound, preferably active for a sufficient period of time, which is used herein for the above purposes.

The metabolites of the compound and a pharmaceutically acceptable salt thereof of the present application, and the prodrugs that may be transformed in vivo into the structures of the compound and a pharmaceutically acceptable salt thereof of the present application also fall within the scope of the claims of the present application.

Preparation Methods

The preparation methods of the compound of Formula (I) of the present invention are described in more detail below, but these specific methods do not constitute any limitation to the present invention. The compound of the present invention can also be conveniently prepared by optionally combining various synthetic methods described in the description or known in the art. Such combination may be easily performed by those skilled in the art to which the present invention belongs.

Usually, in the preparation process, each reaction is usually carried out in an appropriate solvent under the protection of an inert gas at room temperature to 90° C., and the reaction time is usually 2 to 24 hours.

Method I

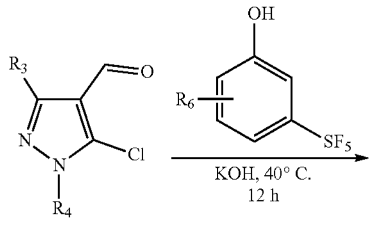

1-1

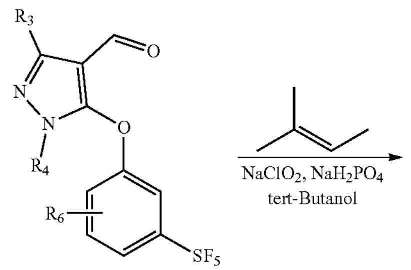

1-2

-continued

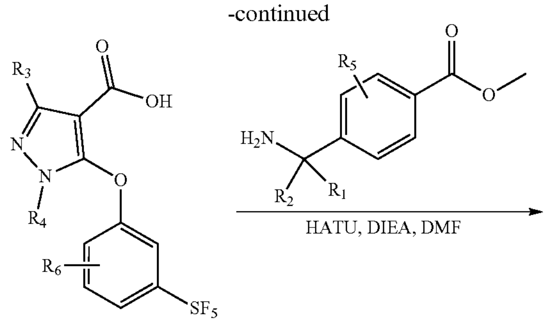

1-3

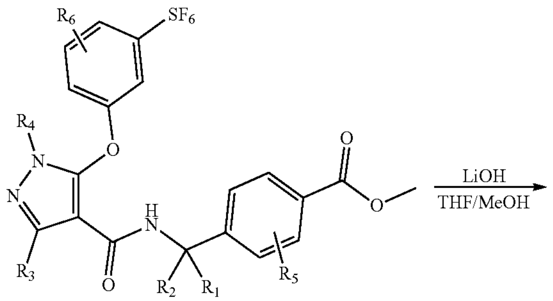

1-4

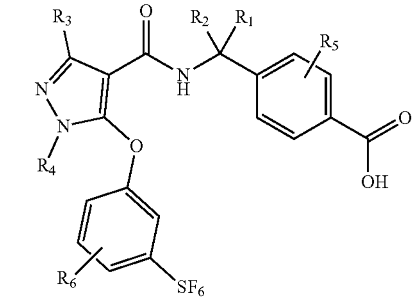

1-5

In Method 1, $R_1$, $R_2$, $R_3$, $R_4$, $R_5$, and $R_6$ have the definitions described in the present invention. The method comprises the steps of:

(i) in an inert solvent, under basic conditions, reacting Compound 1-1 with an o-pentafluorothiophenol derivative to give Compound 1-2;

(ii) in a polar solvent, reacting Compound 1-2 with 2-methyl-2-butene, sodium chlorite, sodium dihydrogen phosphate to give Compound 1-3;

(iii) in an inert solvent, allowing the carboxylic acid in Compound 1-3 to condense with methyl 4-aminomethyl benzoate to give Compound 1-4;

(iv) in a mixed solvent of methanol and tetrahydrofuran, under basic conditions, hydrolyzing the methyl carboxylate in Compound 1-4 into carboxylic acid to give Compound 1-5;

in the above reaction steps, the reaction solvents, reaction temperatures, reaction time, catalysts and so on may be selected according to the specific reactants.

Pharmaceutical Composition and Administration Method

The compounds of the present invention are antagonists of $EP_4$ receptor and thus are expected to be of benefit in the treatment of $EP_4$ receptor-mediated diseases. The pharmaceutical compositions of the present invention are used to prevent and/or treat the following diseases: multiple sclerosis or rheumatoid arthritis, systemic lupus erythematosus, type 1 diabetes, psoriasis, atherosclerosis, Crohn's disease, inflammatory pain, neuropathic pain, migraine-related pain, spondyloarthropathy, skin cancer, breast cancer, colorectal cancer, prostate cancer, kidney cancer, cervical cancer, ovarian cancer, endometrial cancer, glioblastoma, head and neck cancer, medulloblastoma, lung cancer, urethral cancer and other diseases.

In some embodiments, the compounds of the present invention are used as an analgesic. For example, they are useful in the treatment of the following diseases: multiple sclerosis, chronic joint pain (e.g., rheumatoid arthritis, osteoarthritis, rheumatoid spondylitis, gouty arthritis, and juvenile arthritis), musculoskeletal pain; low back and neck pain; sprain and strain; neuropathic pain; sympathetically maintained pain; pain associated with cancer and fibromyalgia; pain associated with migraine; pain associated with influenza or other viral infections such as common cold; rheumatic fever; pain associated with functional bowel disorders such as non-ulcer dyspepsia, non-cardiac chest pain and irritable bowel syndrome; pain associated with myocardial ischemia; postoperative pain; headache; toothache; and dysmenorrhea.

The compound of general formula (I) may be administrated in combination with other known drugs for treating or ameliorating similar conditions. In the case of combination administration, the administration route and dose of the original drug may be kept unchanged, and the compound of Formula I may be administered simultaneously or subsequently. When the compound of Formula I is administrated together with one or several other drugs, the pharmaceutical composition containing one or several known drugs and the compound of Formula I may be preferably used. The combination administration also comprises administration of the compound of Formula I and one or more other known drugs within overlapping periods of time. When the compound of Formula I is administrated in combination with one or several other drugs, the dosage of the compound of Formula I or known drugs may be lower than that of their single administration.

"Pharmaceutically acceptable excipient" and "pharmaceutically acceptable carrier" refer to substances that facilitate the formulation and/or administration and/or absorption by an individual of an active agent and may be included in the composition of the present application without causing significant adverse toxicological effects in the individual. Non-limiting examples of pharmaceutically acceptable carrier and excipient include water, NaCl, physiological saline solution, lactated Ringer's solution, conventional sucrose, conventional glucose, binder, filler, disintegrant, lubricant, coating agent, sweetener, flavoring agent, saline solution (e.g. Ringer's solution), alcohol, oil, gelatin, carbohydrate such as lactose, amylose or starch, fatty acid ester, hydroxymethylcellulose, polyvinylpyrrolidine and pigment, etc. Such formulations may be sterilized and, if desired, mixed with an adjuvant such as lubricant, preservative, stabilizer, wetting agent, emulsifier, salts that affect osmotic pressure, buffer, colorant and/or aroma substance that do not deleteriously react with or interfere with the activity of the compound provided herein. Those of ordinary skill in the art will recognize that other pharmaceutical carriers and excipients are suitable for use with the disclosed compounds.

In some embodiments, the pharmaceutical composition of the present invention may be in solid or liquid form.

The medicament containing the active ingredient (i.e., the compound shown in Formula I) may be suitable oral dosage form, for example tablet, pill, troche, water-soluble or oily suspension, dispersed latex powder or granule, emulsion, hard or soft capsule or syrup or elixirs. The medicament for oral administration may be prepared according to known techniques of manufacturers of pharmaceutical ingredients, and these compositions may comprise one or more of the following agents, such as sweetening agent, flavoring agent, coloring agent and protective agent, in order to provide flavor and delicious pharmaceutical preparations. Tablets contain the active ingredient in admixture with non-toxic pharmaceutically acceptable excipients which are suitable for the manufacture of tablets. Examples of such excipients are inert diluent such as calcium carbonate, sodium carbonate, lactose, calcium phosphate or sodium phosphate; granulating agent, disintegrant such as cornstarch or alginic acid; binder such as starch, gelatin or gum arabic, and lubricant such as magnesium stearate, stearic acid, or talc. The tablets may be uncoated or coated to delay degradation and absorption in the gastrointestinal tract, thereby maintaining activity over a longer period of time.

The active compound may be administered to a subject by any suitable route, including oral, parenteral, inhalation spray, topical, rectal, nasal, buccal, vaginal route, or via an implanted kit. The term "parenteral" as used herein includes subcutaneous, intravenous, intramuscular, intra-articular, intrasynovial, intrasternal, intrathecal, intrahepatic, intralesional and intracranial injection or infusion technique. Preferably, the composition is administered orally, intraperitoneally or intravenously.

The pharmaceutical composition of the present invention suitable for oral administration is typically in solid form in discrete units, for example in the form of tablets, capsules, cachets, powders, granules, lozenges, patches, suppositories, pills, or in liquid form such as liquid preparations, injectable or infusible solutions or suspensions.

The precise amount of the compound to provide a therapeutically effective amount to an individual will depend on the route of administration, the type and severity of the disease and/or condition, and individual characteristics such as general health, age, sex, body weight, and tolerance to the drug. Those of ordinary skill in the art will be able to determine the appropriate dosage based on these and other factors. When administered in combination with an additional therapeutic agent, the "therapeutically effective amount" of any additional therapeutic agent will depend on the type of the drug to be used. Appropriate dosages are known for approved therapeutic agents and can be adjusted by those of ordinary skill in the art according to the individual condition, the type of disease/condition to be treated and the amount of the compound of the present invention used below, for example, the dosage may be those reported in the literature and recommended in Physician's Desk Reference ($57^{th}$ Edition, 2003). Preferably, the compositions should be formulated such that a dose of 0.01-100 mg/kg body weight/day of the inhibitor may be administered to patients receiving these compositions. In some embodiments, the composition of the present invention provides a dosage of 0.01 mg to 50 mg. In other embodiments, dose of 0.1 mg to 25 mg or 5 mg to 40 mg is provided.

Examples of the subject to whom the pharmaceutical composition or therapeutic agent of the present invention is administered include mammals (for example, humans, mice, rats, hamsters, rabbits, cats, dogs, cows, sheep, monkeys, etc.).

The present invention also provides a preparation method of the pharmaceutical composition, comprising the steps of: mixing a pharmaceutically acceptable carrier with the compound of general Formula (I) or a crystal form, a pharmaceutically acceptable salt, a hydrate or a solvate thereof to form the pharmaceutical composition.

The present invention also provides a method of treatment, comprising the steps of: administering the compound of general Formula (I) or a crystal form, a pharmaceutically acceptable salt, a hydrate or a solvate thereof described in the present invention, or administering the pharmaceutical composition described in the present invention to a subject in need of the treatment to selectively inhibit an $EP_4$ receptor.

The present invention has the following main advantages:

(1) The compound of the present invention has better inhibitory activity and selectivity to $EP_4$ receptor.

(2) The compound of the present invention has relatively low toxic and side effects.

(3) The compound of the present invention has better pharmacodynamic and pharmacokinetic properties as well as druggability.

Below in combination with specific examples, the present invention is further illustrated. It should be understood that these examples are only used to illustrate the present invention and are not intended to limit the scope of the present invention. The experimental methods without giving specific conditions in the following examples were usually performed according to conventional conditions such as those described by Sambrook et al., Molecular Cloning: A Laboratory Manual (New York: Cold Spring Harbor Laboratory Press, 1989), or according to the conditions recommended by the manufacturers. Percentages and parts are by weight unless otherwise indicated.

Unless otherwise defined, all professional and scientific terms used herein have the same meanings as commonly understood by those skilled in the art. In addition, any methods and materials similar or equivalent to those described may be applied to the method of the present invention. The preferred implementation methods and materials described herein are for demonstration purposes only.

The structures of the compounds of the present invention were determined by nuclear magnetic resonance (NMR) and liquid chromatography-mass chromatography (LC-MS).

NMR was detected using Bruker AVANCE-400 and Bruker AVANCE-500 nuclear magnetic instruments, and the determination solvents included deuterated dimethyl sulfoxide (DMSO-$d_6$), deuterated acetone ($CD_3COCD_3$), deuterated chloroform ($CDCl_3$) and deuterated methanol ($CD_3OD$) etc., the internal standard adopted tetramethylsilane (TMS), and the chemical shift was measured in parts per million (ppm).

Liquid chromatography-mass chromatography (LC-MS) was detected using Agilent 1260 mass spectrometer. Agilent 1100 high pressure chromatograph (Microsorb 5 micron C18 100x3.0 mm chromatographic column) was used for HPLC measurement.

Thin-layer chromatography silica gel plates used were Qingdao GF254 silica gel plates, TLC adopted 0.15 to 0.20 mm, and preparative thin-layer chromatography adopted 0.4 mm to 0.5 mm. Column chromatography generally used Qingdao silica gel 200-300 mesh silica gel as carrier.

The starting materials in the examples of the present invention were all known and commercially available, or can be synthesized adopting or according to literatures reported in the art.

Unless otherwise specified, all the reactions of the present invention were carried out under the protection of dry inert gas (e.g., nitrogen or argon) and continuous magnetic stirring, and the reaction temperatures were all in degrees Celsius.

The following abbreviations are used throughout the present invention:

THF: Tetrahydrofuran
MeOH: Methanol
HCl: Hydrochloric acid
$Pd(PPh_3)_4$: Tetrakistriphenylphosphine palladium
$K_2CO_3$: Potassium carbonate
AcOK: Potassium acetate
NaOH: Sodium hydroxide
$H_2O$: Water
TEA: Triethylamine
DIEA: N,N-Diisopropylethylamine
DMF: N,N-Dimethylformamide
DMA: N,N-Dimethylacetamide
Py: Pyridine
DCE: 1,2-Dichloroethane
DMSO: Dimethyl sulfoxide
TFA: Trifluoroacetic acid
$NaBH(AcO)_3$: Sodium triacetylborohydride
$Sn_2(Bu\text{-}n)_6$: Hexabutylditin
$AlCl_3$: Aluminum trichloride
CuI: Cuprous iodide
DPPA: Diphenylphosphoryl azide
BuOH: tert-Butanol
$Cs_2CO_3$: Cesium carbonate
$K_3PO_4$: Potassium phosphate
BnBr: Benzyl bromide
$Pd_2(dba)_3$: Tris(dibenzylideneacetone) dipalladium
X-Phos: 2-Dicyclohexylphosphino-2,4,6-triisopropylbiphenyl
EA: Ethyl acetate
$NaHCO_3$: Sodium bicarbonate
DIPEA: N,N-Diisopropylethylamine
HBr: Hydrogen bromide Example 1: Synthesis of Compound 1

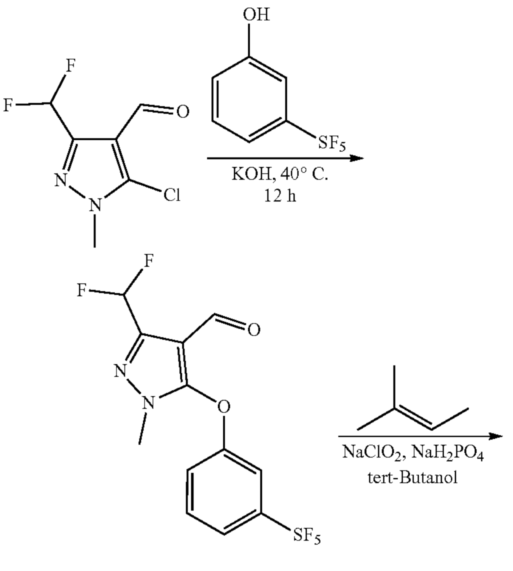

-continued

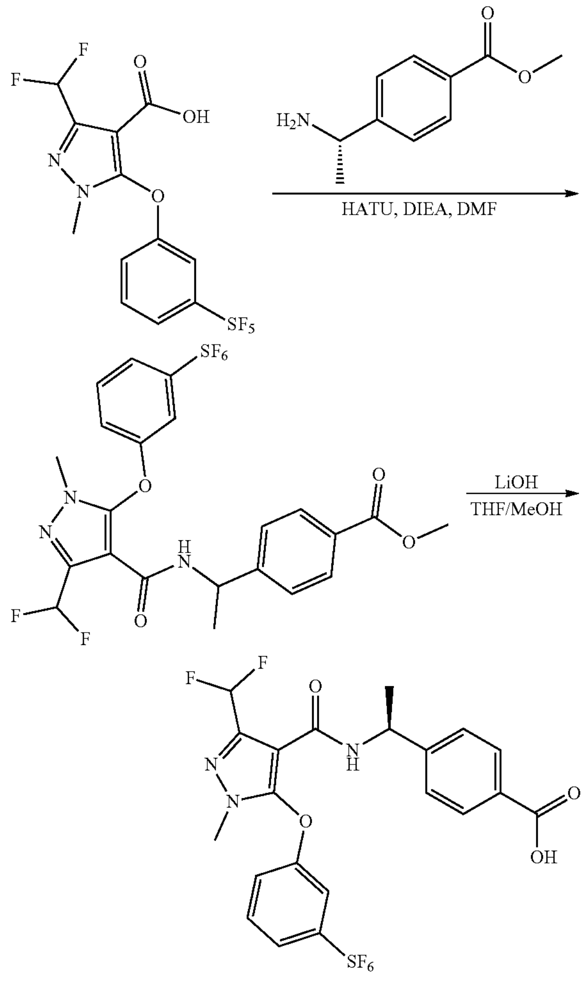

Step 1: Synthesis of 3-(difluoromethyl)-1-methyl-5-(3-(pentafluorothio) phenoxy)-1H-pyrazole-4-carbaldehyde 3-(Pentafluorothio) phenol (0.85 g, 3.85 mmol) was dissolved in anhydrous DMF (5 mL), then potassium hydroxide (0.29 g, 5.14 mmol) was added, and the reaction solution was reacted at room temperature for 20 min. Then 5-chloro-3-(difluoromethyl)-1-methyl-1H-pyrazole-4-carbaldehyde (0.50 g, 2.57 mmol) was added, heated to 40° C. and stirred for 2 h. After monitoring the completion of the reaction, the reaction solution was poured into an appropriate amount of ice water, stirred to precipitate a white solid. The solid was filtered, dissolved in EA, dried by reduced pressure distillation to obtain 0.84 g of 3-(difluoromethyl)-1-methyl-5-(3-(pentafluorothio) phenoxy)-1H-pyrazole-4-carbaldehyde. MS m/z (ESI): 379.3 $[M+H]^+$.

Step 2: Synthesis of 3-(difluoromethyl)-1-methyl-5-(3-(pentafluorothio) phenoxy)-1H-pyrazole-4-carboxylic acid 3-(Difluoromethyl)-1-methyl-5-(3-(pentafluorothio) phenoxy)-1H-pyrazole-4-carbaldehyde (0.84 g, 2.21 mmol) and 2-methyl-2-butene (0.25 g, 3.54 mmol) were dissolved in tert-butanol (6 mL), then sodium chlorite (0.40 g, 4.43 mmol) and sodium dihydrogen phosphate (0.58 g, 4.87 mmol) that were dissolved in water were added. The reaction solution was reacted at room temperature for 12 h. After TLC monitoring the completion of the reaction, the solvent was dried by reduced pressure distillation, the crude product was dissolved in EA, and the organic phase was washed with water, dried by reduced pressure distillation, and then vacuumed using oil pump for 10 min to obtain 0.83 g of pure product 3-(difluoromethyl)-1-methyl-5-(3-(pentafluorothio) phenoxy)-1H-pyrazole-4-carboxylic acid. MS m/z (ESI): 395.3 $[M+H]^+$.

Step 3: Synthesis of methyl 4-(1-(3-(difluoromethyl)-1-methyl-5-(3-(pentafluorothio) phenoxy)-1H-pyrazole-4-carboxamido)ethyl)benzoate 3-(Difluoromethyl)-1-methyl-5-(3-(pentafluorothio) phenoxy)-1H-pyrazole-4-carboxylic acid (0.83 g, 2.11 mmol) was dissolved in anhydrous DMF (6 mL), HATU (0.96 g, 2.53 mmol) was added under ice bath, and then DIEA (0.82 g, 6.33 mmol) was added into the system, stirred at room temperature for 10-30 min. Then methyl(S)-4-(1-aminoethyl)benzoate (0.42 g, 2.32 mmol) was added, and the resulting system was reacted at room temperature for 1 h. After TLC monitoring the completion of the reaction, the system was poured into ice water to precipitate a solid. The solid was dissolved in EA, dried by reduced pressure distillation. The crude product was subjected to silica gel column chromatography with EA/PE=1:3 to obtain 1.04 g of pure product methyl 4-(1-(3-(difluoromethyl)-1-methyl-5-(3-(pentafluorothio) phenoxy)-1H-pyrazole-4-carboxamido) ethyl)benzoate. MS m/z (ESI): 556.5 $[M+H]^+$.

Step 4: Synthesis of 4-(1-(3-(difluoromethyl)-1-methyl-5-(3-(pentafluorothio) phenoxy)-1H-pyrazole-4-carboxamido)ethyl)benzoic acid Methyl 4-(1-(3-(Difluoromethyl)-1-methyl-5-(3-(pentafluorothio) phenoxy)-1H-pyrazole-4-carboxamido)ethyl) benzoate (1.04 g, 1.87 mmol) was dissolved in THF/$H_2O$ (3:1, 12 mL), then lithium hydroxide (0.09 g, 3.74 mmol) was added, stirred at 35° C. for 16 h. After TLC monitoring the completion of the reaction, the solvent was dried by reduced pressure distillation, water was added, and dilute hydrochloric acid was added to adjust the pH value to about 2~3, a white solid was precipitated, during the process. The solid was filtered, and dissolved in EA. The aqueous phase was extracted twice with EA, and then the organic phases were combined, dried by reduced pressure distillation. The crude product was subjected to silica gel column chromatography with EA/PE=1:5 to obtain 0.55 g of pure product 4-(1-(3-(difluoromethyl)-1-methyl-5-(3-(pentafluorothio) phenoxy)-1H-pyrazole-4-carboxamido)ethyl)benzoic acid (Compound 1). MS m/z (ESI): 542.4 $[M+H]^+$.

$^1$H NMR (500 MHZ, DMSO) § 12.79 (s, 1H), 8.16 (d, J=7.4 Hz, 1H), 7.75 (d, J=1.8 Hz, 2H), 7.70 (d, J=2.2 Hz 2H), 7.62 (t, J=8.3 Hz 1H), 7.22 (m, 1H), 7.12 (m, 1H), 7.11 (m, 1H), 7.09 (m, 1H), 4.97 (m, 1H), 3.77 (s, 3H), 1.17 (m, 3H).

Example 2

Using a method similar to that of Example 1, Compound 2 was prepared.

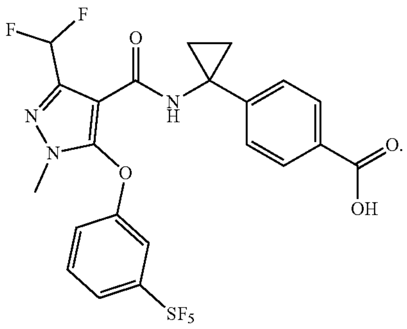

2

Example 3

Using a method similar to that of Example 1, Compound 3 was prepared.

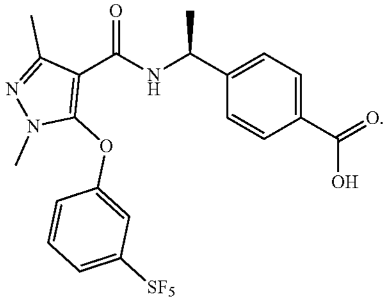

3

Test of Biological Activity (a) Antagonist Activity Against $EP_4$ Receptor by cAMP Assay:

Experimental method: Flpin-CHO-$EP_4$ cells (8000/well) were seeded into a 384-well plate (6007680-50, PE) with an assay buffer (1×HBSS+20 mM HEPES+0.1% BSA+500 UM IBMX). 8× compound working solution was prepared with the assay buffer. 2.5 μL of 8× compound working solution was added to each well of the cell plate according to the plate map, and incubated at 37° C. for 10 min. 8×$PGE_2$ (400 nM) was prepared the assay buffer. 2.5 μL of 8×$PGE_2$ was added to each well of the cell plate and incubated at 37° C. for 30 minutes. Eu-CAMP tracer (1/50) was diluted with a lysis buffer and 10 μL was added to per well of the detection plate. Ulight-anti-CAMP (1/150) was diluted with the lysis buffer and 10 μL was added to per well of the detection plate, and incubated at room temperature for 1 h. The 665 nm and 615 nm wavelength signals were read on an Envision 2105 plate reader. The results were shown in Table 1.

TABLE 1

| Compound | Starting concentration (μM) | Dilution factor (*) | $IC_{50}$ (nM) |
|---|---|---|---|
| Control compound | 5 | 4 | 54.630 |
| Example 1 | 5 | 4 | 6.587 |

Control compound

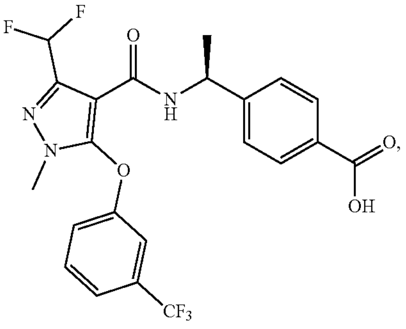

Example 1

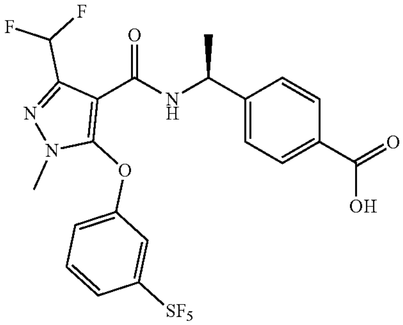

After testing, the compound of the example of the present invention showed excellent $EP_4$ inhibitory activity.

All documents mentioned in the present invention are incorporated by reference in the present application as if each were individually incorporated by reference. In addition, it should be understood that after reading the above teachings of the present invention, those skilled in the art can make various changes or modifications to the present invention, and these equivalent forms also fall within the scope defined by the appended claims of the present application.

What is claimed is:

1. A compound of Formula I or a pharmaceutically acceptable salt, a hydrate, a solvate, a stereoisomer, an isotopic compound or a prodrug thereof;

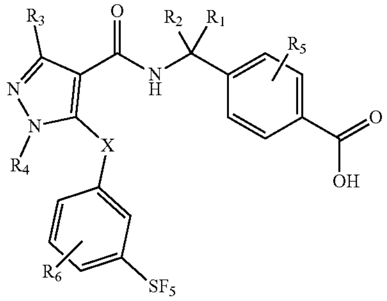

(I)

wherein, $R_1$ and $R_2$ are each independently selected from the group consisting of: H, unsubstituted or halogen-substituted $C_1$-$C_4$ alkyl;

or $R_1$ and $R_2$ form a $C_3$-$C_6$ cycloalkyl together with the carbon atom to which they are connected;

$R_3$ is unsubstituted or halogen-substituted $C_1$-$C_4$ alkyl;

$R_4$ is unsubstituted or halogen-substituted $C_1$-$C_4$ alkyl;

$R_5$ is selected from the group consisting of: hydrogen, halogen, $C_1$-$C_4$ alkyl and $C_1$-$C_4$ alkoxy; and $R_6$ is absent or selected from the group consisting of: halogen, unsubstituted or halogen-substituted $C_1$-$C_4$ alkyl, and unsubstituted or halogen-substituted $C_1$-$C_4$ alkoxy, X is O.

2. The compound or a pharmaceutically acceptable salt, a hydrate, a solvate, a stereoisomer, an isotopic compound or a prodrug thereof according to claim 1, wherein one of $R_1$ and $R_2$ is H, and the other is unsubstituted or halogen-substituted $C_1$-$C_4$ alkyl.

3. The compound or a pharmaceutically acceptable salt, a hydrate, a solvate, a stereoisomer, an isotopic compound or a prodrug thereof according to claim 1, wherein $R_3$ is methyl, monofluoromethyl, difluoromethyl or trifluoromethyl.

4. The compound or a pharmaceutically acceptable salt, a hydrate, a solvate, a stereoisomer, an isotopic compound or a prodrug thereof according to claim 1, wherein $R_4$ is methyl.

5. The compound or a pharmaceutically acceptable salt, a hydrate, a solvate, a stereoisomer, an isotopic compound or a prodrug thereof according to claim 1, wherein the prodrug is an ester formed by the compound of Formula I and $C_1$-$C_4$ alkyl-OH.

6. The compound or a pharmaceutically acceptable salt, a hydrate, a solvate, a stereoisomer, an isotopic compound or a prodrug thereof according to claim 1, wherein the compound of Formula I is selected from the group consisting of:

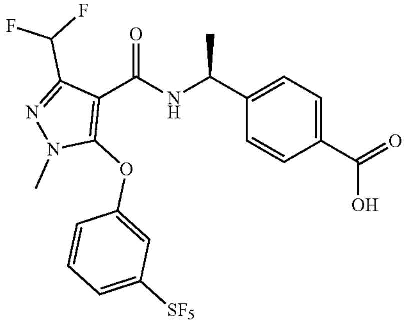

1

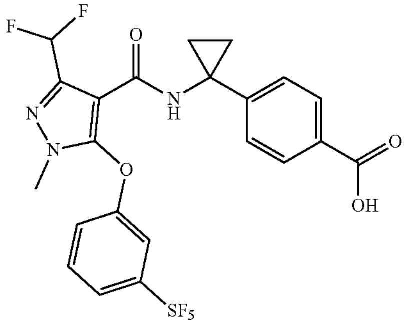

2

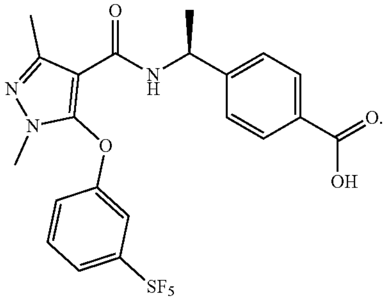

3

7. A pharmaceutical composition, comprising the compound or a pharmaceutically acceptable salt, a hydrate, a solvate, a stereoisomer, an isotopic compound or a prodrug thereof according to claim 1, and a pharmaceutically acceptable carrier or diluent.

8. A method for inhibiting $EP_4$ receptor activity in a cell or a subject, comprising administering to the subject in need thereof an effective amount of the compound or pharmaceutically acceptable salt, hydrate, solvate, stereoisomer, isotopic compound or prodrug thereof according to claim 1, or contacting an effective amount of the compound or pharmaceutically acceptable salt, hydrate, solvate, stereoisomer, isotopic compound or prodrug thereof according to claim 1 with the cell.

9. A method for preventing and/or treating a disease associated with an $EP_4$ receptor, comprising administering to a subject in need thereof an effective amount of the compound or pharmaceutically acceptable salt, hydrate, solvate, stereoisomer, isotopic compound or prodrug thereof according to claim 1.

10. The method according to claim 9, wherein the disease associated with $EP_4$ receptor is selected from the group consisting of acute and chronic pain, osteoarthritis, rheumatoid arthritis and cancer.

* * * * *